(12) United States Patent
Maslanka et al.

(10) Patent No.: US 12,082,799 B2
(45) Date of Patent: *Sep. 10, 2024

(54) IMPLANT, MEDICAL IMPLANT, AND METHOD FOR DELIVERY OF A MEDICAL IMPLANT

(71) Applicants: Occlutech GmbH, Jena (DE); Maslanka Patentverwaltung GmbH, Tuttingen (DE)

(72) Inventors: Herbert Maslanka, Tuttingen (DE); Stevan Nielsen, Jena (DE)

(73) Assignees: Maslanka Patentverwaltung Gmbh, Tuttingen (DE); Occlutech Gmbh, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/063,035

(22) Filed: Dec. 7, 2022

(65) Prior Publication Data

US 2023/0107869 A1    Apr. 6, 2023

Related U.S. Application Data

(63) Continuation of application No. 17/457,031, filed on Nov. 30, 2021, now Pat. No. 11,571,198, which is a
(Continued)

(30) Foreign Application Priority Data

Apr. 16, 2009  (EP) ..................... 09158098
May 6, 2009    (EP) ..................... 09159586

(51) Int. Cl.
*A61B 17/00* (2006.01)
*A61B 17/12* (2006.01)
(Continued)

(52) U.S. Cl.
CPC .... *A61B 17/0057* (2013.01); *A61B 17/12022* (2013.01); *A61B 17/12109* (2013.01);
(Continued)

(58) Field of Classification Search
CPC .......... A61B 17/0057; A61B 17/12022; A61B 17/12109; A61B 17/3468;
(Continued)

(56) References Cited

U.S. PATENT DOCUMENTS 4,817,600 A    4/1989  Herms et al.
4,867,745 A    9/1989  Patel
(Continued)

FOREIGN PATENT DOCUMENTS

EP         0 698 373 A2    2/1996
WO    WO 2009/016265 A2   2/2009

*Primary Examiner* — Jocelin C Tanner
(74) *Attorney, Agent, or Firm* — Inskeep IP Group, Inc.

(57) ABSTRACT

An intravascular delivery device is disclosed comprising a delivery wire having a proximal and a distal end and an interior lumen extending there between and wherein said distal end comprises a connection interface adapted to matingly interlock with a proximal end portion of a medical implantable device, wherein said delivery device comprises a locking unit arranged to secure said connection interface in a locking position in which said medical implant is pivotably locked before a controlled release.

26 Claims, 15 Drawing Sheets

Related U.S. Application Data continuation of application No. 15/884,713, filed on Jan. 31, 2018, now Pat. No. 11,213,282, which is a continuation of application No. 13/264,728, filed as application No. PCT/EP2010/056140 on May 6, 2010, now Pat. No. 9,993,234.

(51) Int. Cl.
    *A61B 17/34*      (2006.01)
    *A61F 2/95*      (2013.01)

(52) U.S. Cl.
    CPC ............ *A61B 17/3468* (2013.01); *A61B 2017/00477* (2013.01); *A61B 2017/00575* (2013.01); *A61B 2017/00592* (2013.01); *A61B 2017/00606* (2013.01); *A61B 2017/00623* (2013.01); *A61B 2017/12054* (2013.01); *A61B 17/12113* (2013.01); *A61B 17/12122* (2013.01); *A61B 17/12172* (2013.01); *A61F 2002/9505* (2013.01)

(58) Field of Classification Search
    CPC ........ A61B 17/12113; A61B 17/12122; A61B 17/12172; A61B 2017/00575; A61B 2017/00592; A61B 2017/00606; A61B 2017/00623; A61B 2017/12054; A61F 2002/9505

See application file for complete search history.

(56) References Cited

U.S. PATENT DOCUMENTS

| | | |
|---|---|---|
| 5,217,484 A | 6/1993 | Marks |
| 5,407,243 A | 4/1995 | Riemann |
| 6,355,052 B1 | 3/2002 | Neuss et al. |
| 6,468,290 B1 | 10/2002 | Weldon et al. |
| 7,344,553 B2 | 3/2008 | Opolski |
| 9,993,234 B2* | 6/2018 | Maslanka .......... A61B 17/0057 |
| 11,213,282 B2* | 1/2022 | Maslanka ........ A61B 17/12109 |
| 11,571,198 B2* | 2/2023 | Maslanka .......... A61B 17/0057 |
| 2003/0045901 A1 | 3/2003 | Opolski |
| 2003/0181945 A1 | 9/2003 | Opolski et al. |
| 2004/0176797 A1* | 9/2004 | Opolski ........... A61B 17/12109 |
| | | 606/213 |
| 2007/0112381 A1 | 5/2007 | Figulla et al. |
| 2007/0186933 A1 | 8/2007 | Domingo et al. |
| 2009/0132033 A1 | 5/2009 | Maurer et al. |

* cited by examiner

IMPLANT, MEDICAL IMPLANT, AND METHOD FOR DELIVERY OF A MEDICAL IMPLANT

RELATED APPLICATIONS

This application is a continuation and claims benefit and priority to patent application Ser. No. 17/457,031 filed Nov. 30, 2021, entitled Implant, Medical Implant, And Method For Delivery Of A Medical Implant, which is a continuation and claims benefit and priority to patent application Ser. No. 15/884,713 filed Jan. 31, 2018, entitled Implant, Medical Implant, And Method For Delivery Of A Medical Implant (Now U.S. Pat. No. 11,213,282 issued Jan. 4, 2022), which is a continuation of and claims benefit and priority to U.S. patent application Ser. No. 13/264,728, filed Jan. 31, 2012, entitled Implant, Medical Implant, And Method For Delivery Of A Medical Implant (now U.S. Pat. No. 9,993,234 issued Jun. 12, 2018), which claims benefit and priority to International Patent Application No. PCT/EP2010/056140, International Filing Date May 6, 2010, entitled Implant, Medical Implant, And Method For Delivery Of A Medical Implant, which claims benefit and priority to European Patent Application No. EP09158098.5 filed Apr. 16, 2009 entitled Implant, Medical Implant, And Method For Delivery Of A Medical Implant, and to European Patent Application No. EP09159586.8 filed May 6, 2009 entitled Implant, Medical Implant, And Method For Delivery Of A Medical Implant, all of which are hereby incorporated herein by reference in their entireties.

FIELD OF THE INVENTION

This invention pertains in general to the field of medical implants and delivery devices for such implants, as well as methods for transluminal delivery of medical devices into a body

BACKGROUND OF THE INVENTION

Various ways of deployment of a medical implants within a patient's cardiovascular system are known. However, known devices and methods have a number of drawbacks.

For instance WO 97/42878 discloses a medical implant having an end for threadably attachment to a delivery wire. WO 2009/016265 of the same applicant as the present invention discloses a method for producing a connection between two components of a medical implant which preferably are composed of different materials which cannot be welded to one another is described. Furthermore, a medical implant which is produced according to the method is described. Moreover, the medical implant comprises a connection interface whereon said medical implant is detachable from an introduction wire or introduction implement. The attachment to the introduction wire or introduction implement is also based on threaded attachment to an adapter that is put over e.g. a welded end of a bundle of wires of an implant.

Treaded attachment may in certain clinical situations not unlock inside the body, when the implant is positioned. Consequently the implant has to be removed from the body together with delivery wire. This increases the time of surgery and related costs unnecessarily. Also, patient safety is reduced due to such unintended and undesired procedure.

Furthermore, the threaded attachment may loosen before implant is at final position and is unintentionally released in the patient's body. Loosening may for instance be initiated when the implant is collapsed in a catheter and the delivery wire is rotated during delivery relative a surrounding catheter. This may be done unintentionally by the human factor. Embolies may be caused by the loosened medical devices uncontrollably released in the body.

Both above failures have dire consequences for the patient and the health care system. Patient risk is increased.

Also, when the medical device is released from the catheter, and still attached to the threaded delivery wire, the medical implant is subject to bending, relative the longitudinal axis of the delivery wire, at least in certain anatomical positions, due to the nature of threaded attachment involving a directed bore and mating threads. This is for instance the case in the heart where delivery is difficult, e.g. perpendicular to a septal wall having an opening to be closed by the implant. This may affect the material of the device leading to fatigue of the device.

The implant is also affected by a force at release which either transposes through the medical implant and may then have a negative impact on the surrounding tissue or the medical implant inherently grasp the force and is affected as described above.

United States patent application 2003/0181945 ('145) discloses a coupling system that is disposed at the distal end of an interventional delivery system for coupling to an implant. The coupling device has a first and second prong connected at one end. The other end of the prongs open or close to release or trap an object, e.g., a bead tethered from an implant. A slot at the distal end of the coupling device allows extra degrees of flexibility for the coupling device. However, implant pivoting in a plane along the longitudinal axis of the coupling device", according to '145 paragraph [0010]. Hence, the pivoting motion is restricted to a single plane only and the degree of flexibility still very limited.

United States patent application 2003/045901 discloses another flexible delivery system for a medical implant avoiding. The system has a wire formed from a plurality of layered strands yielding a reduced bending stiffness for improved maneuverability with no reduction in overall tensile strength compared to delivery systems using a single wire and of comparable diameter. However, the system does neither allow for the desired delivery flexibility mentioned above nor does it lock the implant in relation the delivery device in a reliable manner. The implant may for instance move in longitudinal direction during delivery when manipulating the delivery catheter in relation to the implant. Exact delivery to a desired location may thus be complicated in practice.

United States patent application US2004/176797 discloses a magnetic attachment system which again raises locking issues as well as release issues as the implant may not be released from the magnetic connection in a precise controlled manner in the patient's body. Moreover flexibility in terms of a movement degree of freedom of the implant while attached to the delivery device is limited.

Also, a more flexible delivery is desired in terms of adjustments of the device used and applied methods, due to the fact that different patients are anatomically slightly different to one another and that the deficiency to be treated is most often individual and unique for each patient treated.

Thus, there is a need for a deployment device which adjusts for differences in the cardiovascular system between patients still allowing a secure deployment of a medical implant.

Hence, an improved delivery device or system and a method would be advantageous. Also, a medical implant facilitating such improved delivery would be advantageous.

Hence, an improved delivery device or system, medical implant, and a method would be advantageous and in particular allowing for increased flexibility, cost-effectiveness, and/or patient safety would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device, aggregate, and a method according to the appended patent claims.

Further embodiments of the invention are defined in the dependent claims, wherein features for the second and subsequent aspects of the invention are as for the first aspect mutatis mutandis.

More particularly the invention relates to an apparatus for delivering of an occlusion device, and more particularly to intravascular delivery device for delivery of an occlusion device in the cardiovascular system.

Some embodiments of the invention provide for flexible delivery of a medical implant to anatomically difficult to reach sites in a body of a human or animal.

Some embodiments of the invention also provide for secure delivery of a medical implant.

The new delivery system allows significant improvements in product handling. Before release of the occluder, the system allows a tilted angle of up to approximately 45 degrees without any stress or pull on the implant. Especially in challenging cases this feature has proven vital.

This allows the product to be placed in the final position without any adverse pull from a delivery wire. The safe-handling attachment system avoids any risk of unintended release during handling and allows a safe pull back into the catheter should the implantation be interrupted.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
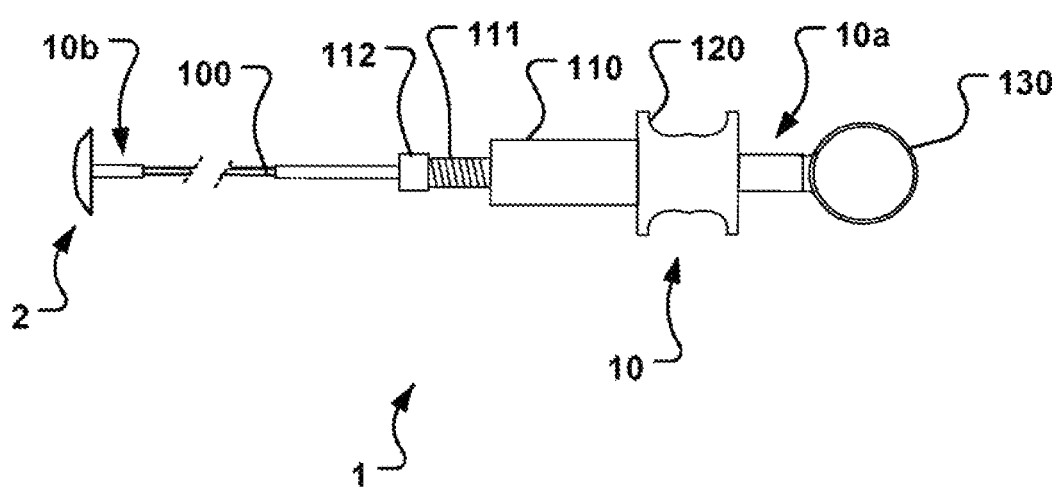
FIG. 1 is assembly view of kit.
Figure 2:
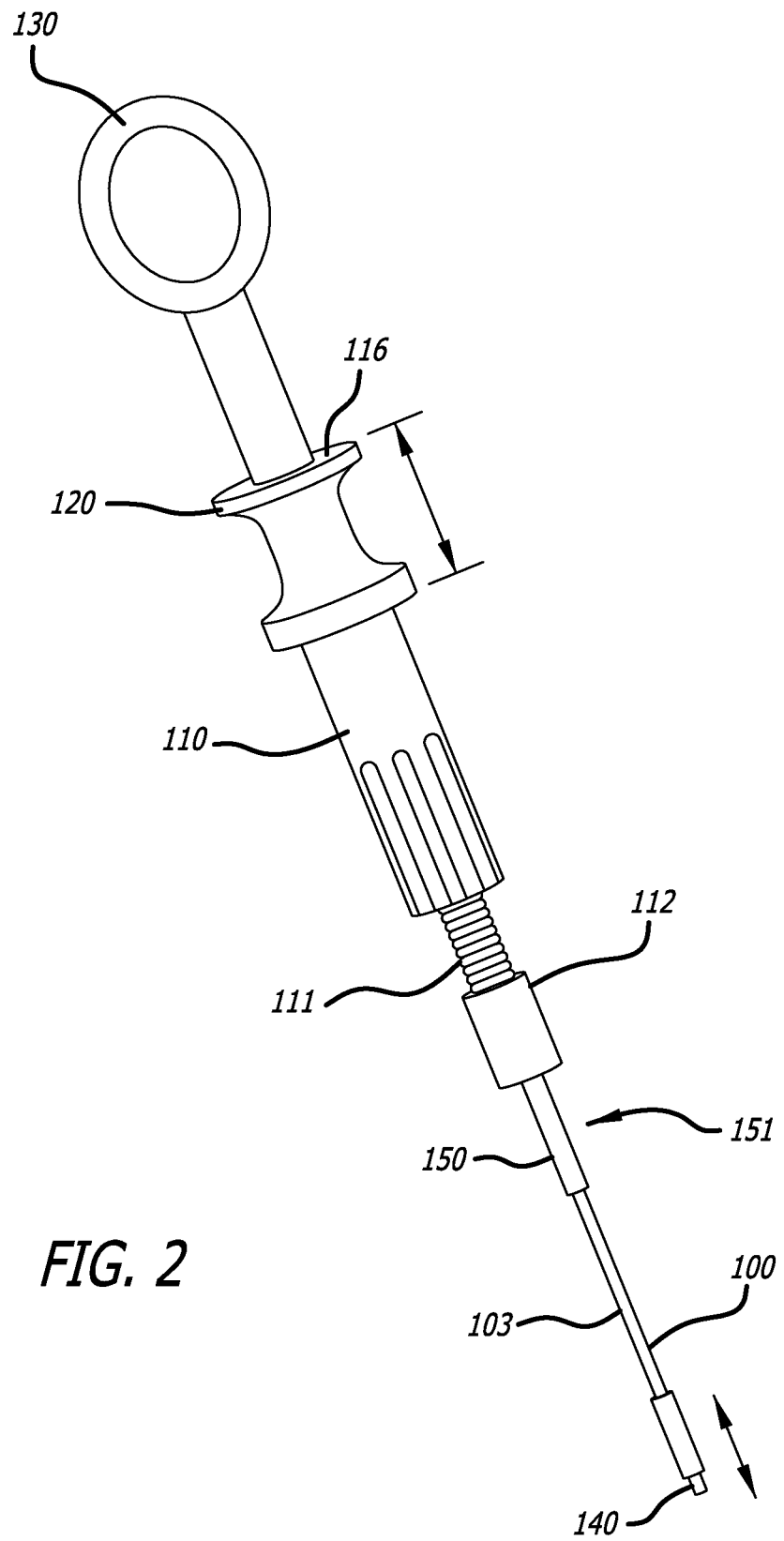
FIG. 2 is a rendered graphical composition.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a septal occluder. However, it will be appreciated that the invention is not limited to this application but may be applied to many other medical implantable devices, including for example filters, stents, left atrial appendage (LAA) occluders, aneurysm treatment devices, grafts, etc.

Figure 3:
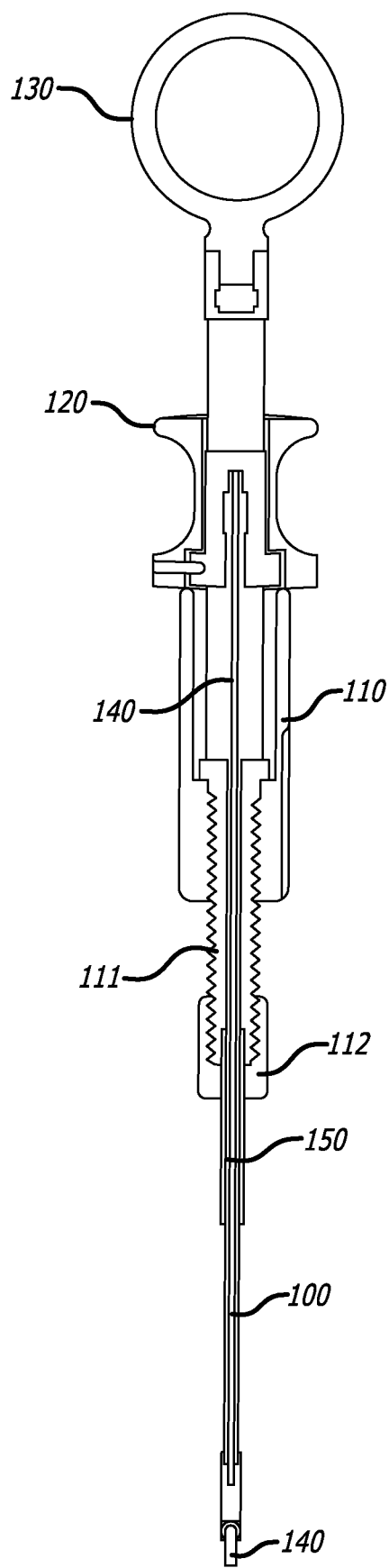
FIG. 3 is a cross-sectional view of the device.

An intravascular delivery device 1 comprises a delivery wire 100 having a proximal 10a and a distal end 10b and an interior lumen 151 extending there between (FIG. 3). The distal end 10b comprises a connection interface 140 adapted to matingly interlock with a proximal end portion 200 of a medical implantable device 2. The delivery device comprises a locking unit 110 arranged to secure the connection interface in a locking position.

The medical device is thus pivotably locked before a controlled release. Pivotably locked means that the medical device is securely attached to the distal end of the delivery device, while it still is able to move in a certain degree of freedom in relation to a longitudinal axis of the distal end of the delivery device. The device is longitudinally locked, but pivotably movable in a radial plane in relation to the delivery device. A degree of freedom is for instance rotatable around the longitudinal axis or tiltable in relation thereto, while being longitudinally locked in relation to the delivery device. This is described in more detail below and allows for a precise yet flexible delivery of the device to a desired target location.

In an embodiment, the intravascular delivery device comprises a locking wire 150 arranged moveably within the lumen 151 of the delivery wire 100 for relative longitudinal movement therein, the locking wire having a distal end comprising a holding structure 141, whereby the holding structure is axially moveable relative the delivery wire 100 between the locking position (FIG. 15b) at which the delivery wire encloses the holding structure and a second position at which the holding structure at least partly protrudes beyond the distal end of the delivery wire (FIG. 13,15a) such that the connection interface unlocks and the medical implantable device is controllably released.

In an embodiment, the medical implantable device is an occlusion device for occluding a selected site in a body. The medical implantable device may be collapsible or expandable, such as self expandable. The medical implantable device 2 may thus be advantageously and securely delivered to a target site via a lumen of the body. At the target site, the device is moved forward out of the catheter, but still securely attached to the delivery wire at the connection interface 140.

The occlusion device is for instance an ASD or PFO occluder for septal occlusion.

The occlusion device is for instance an atrial appendage occluder in other embodiments.

In this relation, for instance a first expanded diameter of the medical implantable device 2 may be positioned on a distal side of an opening in a wall, such as a septal or atrial wall. Then a second expanded diameter of the medical implantable device 2 may be positioned on a proximal side of the opening in the wall. Thus the opening is reliable occluded when the device is grown into the tissue of the wall, e.g. by endothelisation.

Positioning in this anatomically demanding delivery application is facilitated by the delivery device of the present embodiments.

Figure 9A:
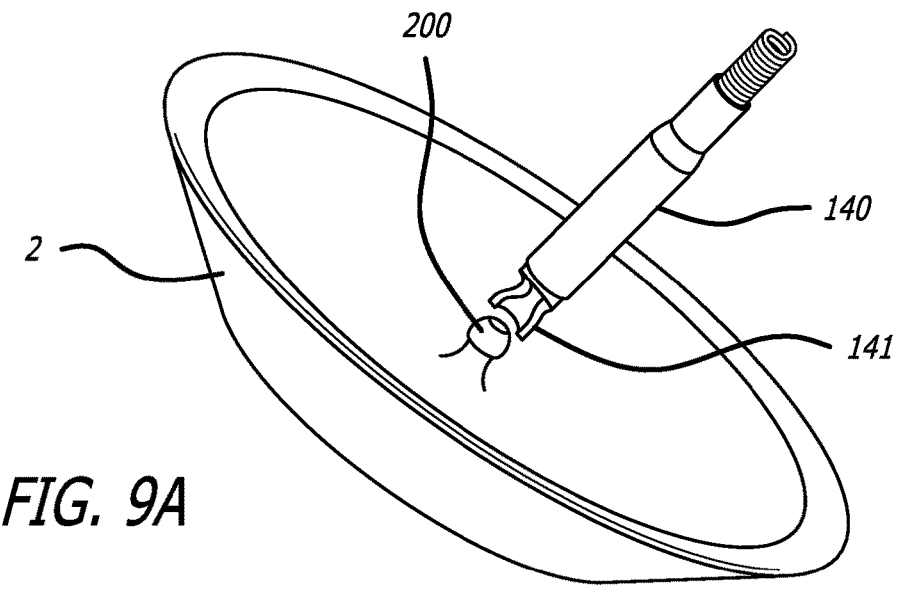
FIG. 9A is a schematic view illustrating another embodiment of the invention of interlocking a medical implant.
Figure 9B:
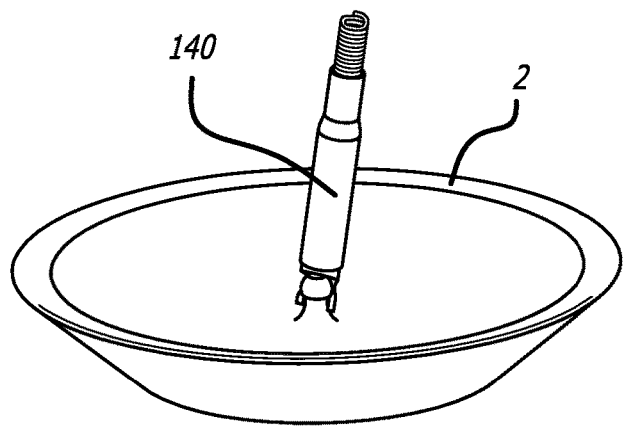
FIG. 9B is a schematic view illustrating another embodiment of the invention of interlocking a medical implant.
Figure 9C:
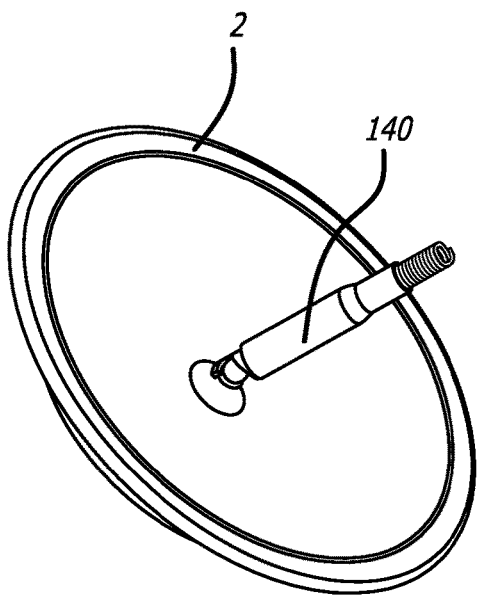
FIG. 9C is a schematic view illustrating another embodiment of the invention of interlocking a medical implant.

However, the device has to be reliably released from the delivery device 1. To this end, a locking unit 110 is unlocked. Here by threaded movement from the locked position (FIG. 4A) to the unlocked position (FIG. 4B). Alternatively, or in addition to threaded locking, other locking units may be provided, such as a latch, spring latch, cap, cover, lid, seal, enclosure, etc. The internal locking wire 150 in the lumen may now be moved forward to push the holding unit 141 at the connection interface out of a sleeve 150 thereof. As can be seen in FIG. 9 for instance, the medical implantable device is now free for release.

During delivery, the medical implantable device 2, when expanded out of the catheter, and also during delivery inside the catheter is rotatably free and may pivot both axially and radially. This increases flexibility during delivery through narrow passages of the lumen for delivery. In addition, when expanded out of the catheter, but still movably locked to the connection interface, the medical implantable device 2 may rotate freely and pivot/tilt both axially and radially, see e.g. FIG. 10 or 11. This provides a large degree of flexibility during delivery and adaptation to different anatomical situations at the target site of the medical implantable device 2.

In an embodiment, the connection interface holding the medical implantable device provides for an axial flexibility such that the medical implantable device may tilt relative the longitudinal axis of the delivery device.

Tilting angles of approximately 45 degrees are thus obtainable.

Figure 13:
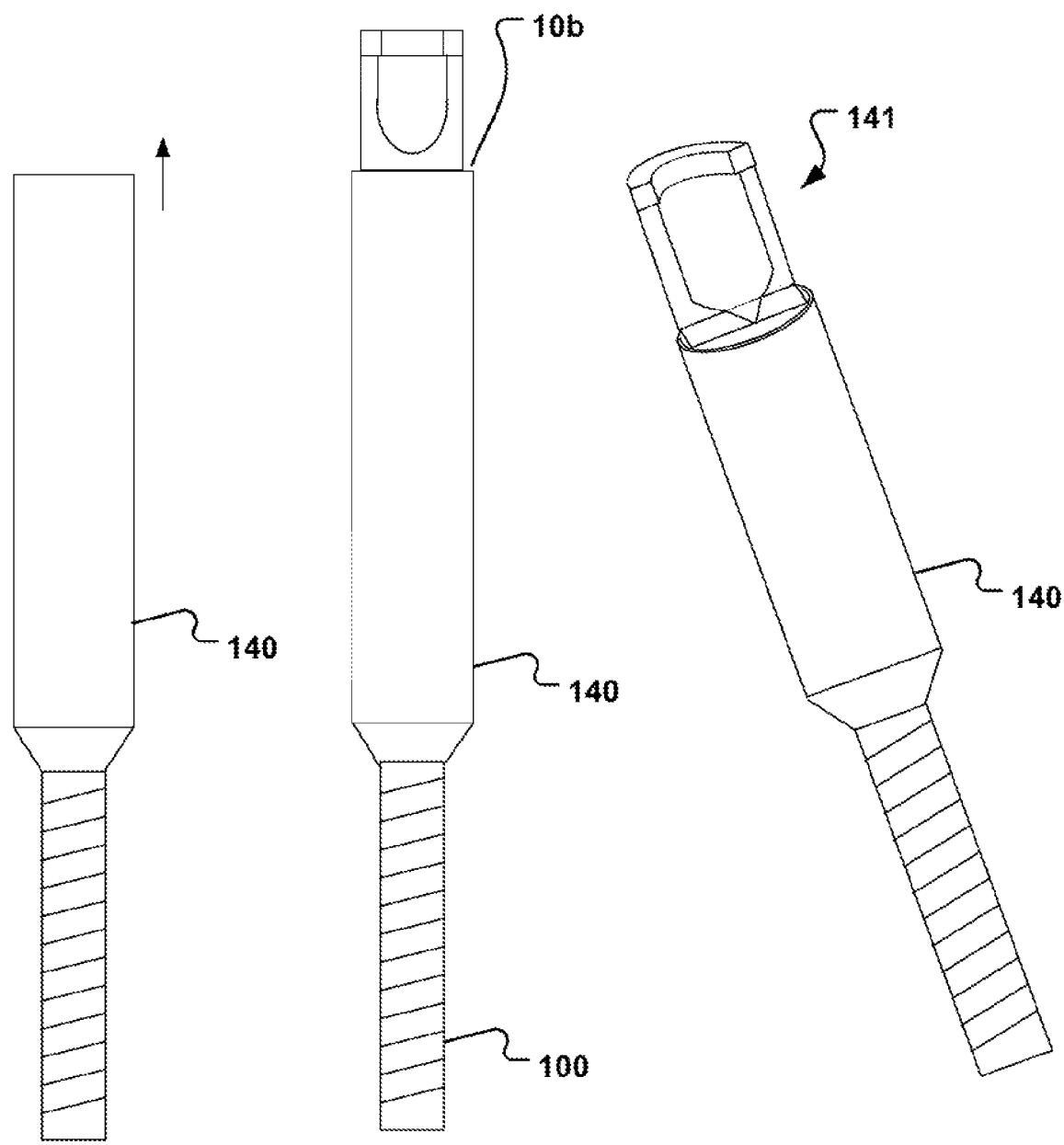
FIG. 13 is an illustration of a holding unit in various positions between locking and release.

In an embodiment, the holding structure 141 is provided radially enlarged to at least partly contact the interior lumen of the distal end of the delivery wire, see e.g. FIG. 13.

Figure 12:
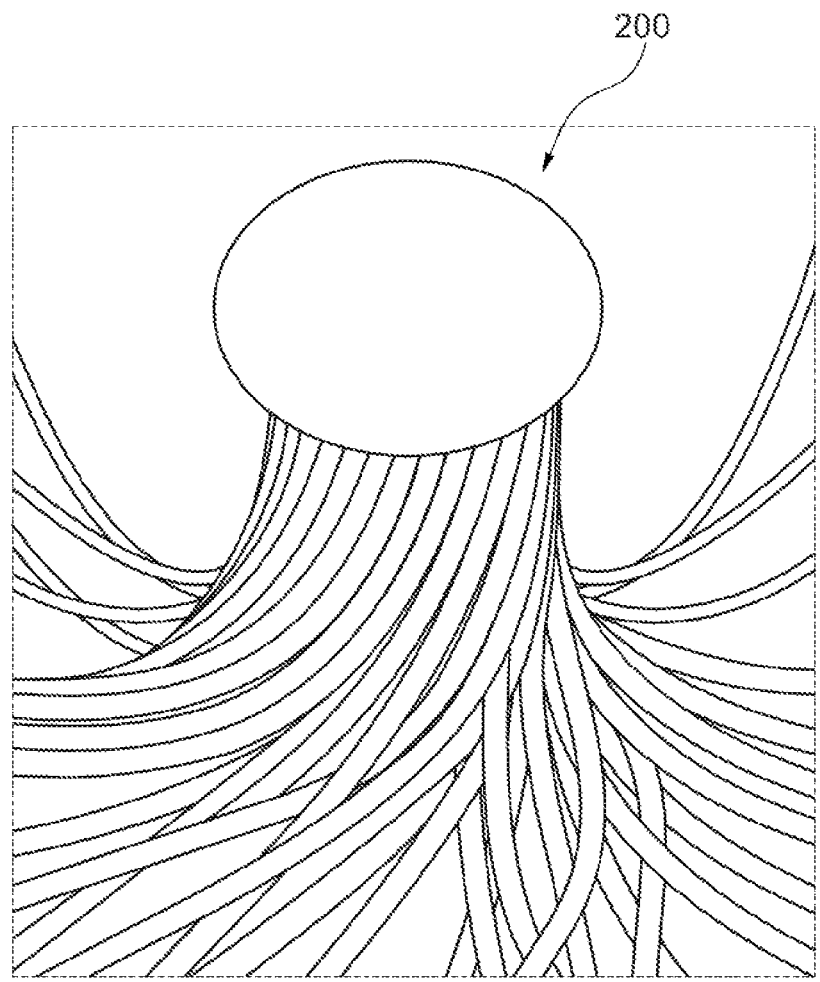
FIG. 12 is an illustration of an end of a medical implantable device.

The holding structure may have a distal recess into which a bundle of wires snugly fits. When the bundle of wires has a thickening, e.g. the spherically shaped end as shown in FIG. 12, it interlocks with the holding unit, once this is drawn into the sleeve 145.

Locking of the medical device 2 to the holding unit is provided by a positive fit which allows for a degree of free movement relative the delivery wire when locked.

In an embodiment, the distal part of the holding structure 141 is bowl-shaped and has a recess in the edge of the bowl-shaped portion at the distal end of the holding structure for receiving a portion of the medical implantable device. The recess may receive a neck of the medical implantable device. The bowl shaped portion, together with a welded clot at the proximal end 200 having a substantially spherical shape (FIG. 12) provides thus for the pivotal movement in an embodiment.

In an embodiment, the bowl-shaped recess is configured to enclose the proximal end portion of the medical implantable device at least partly.

Figure 7:
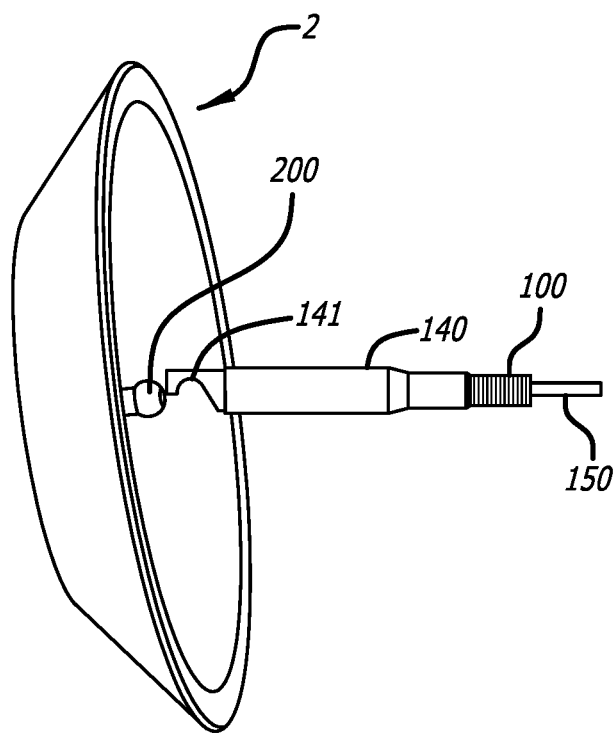
FIG. 7 is a schematic view illustrating the principle of locking a detachable device used in an embodiment of the invention.
Figure 8:
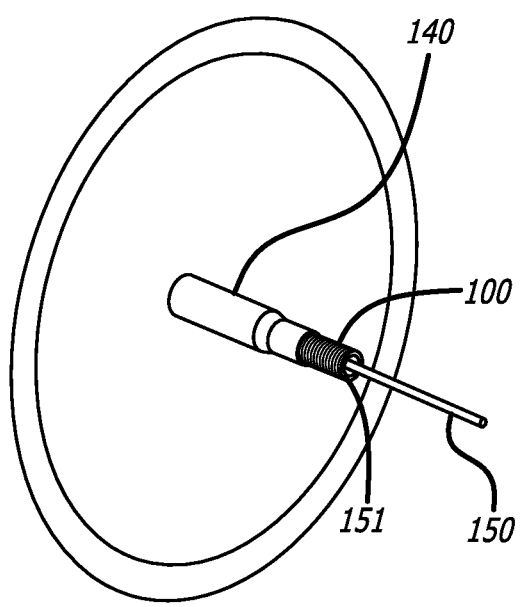
FIG. 8 is a schematic view of an interlocked device.
Figure 10A:
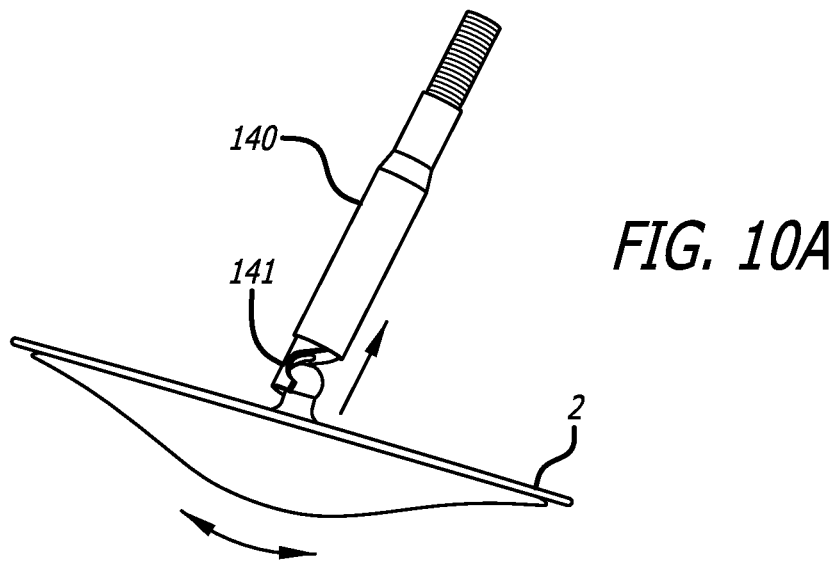
FIG. 10A is a schematic view showing yet a further embodiment of the invention of interlocking medical implant.
Figure 10B:
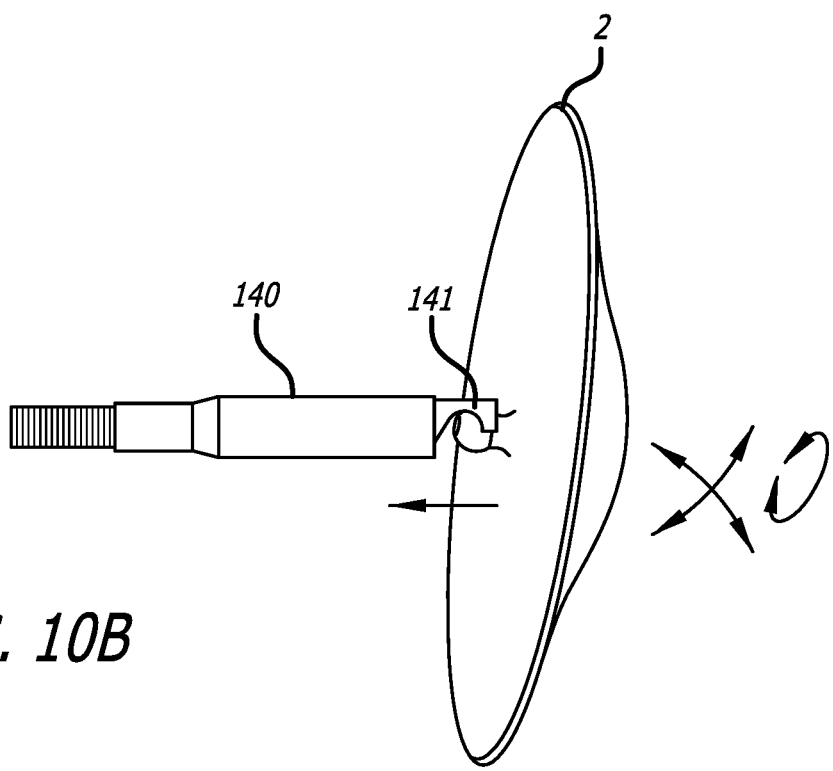
FIG. 10B is a schematic view showing yet a further embodiment of the invention of interlocking medical implant.
Figure 11A:
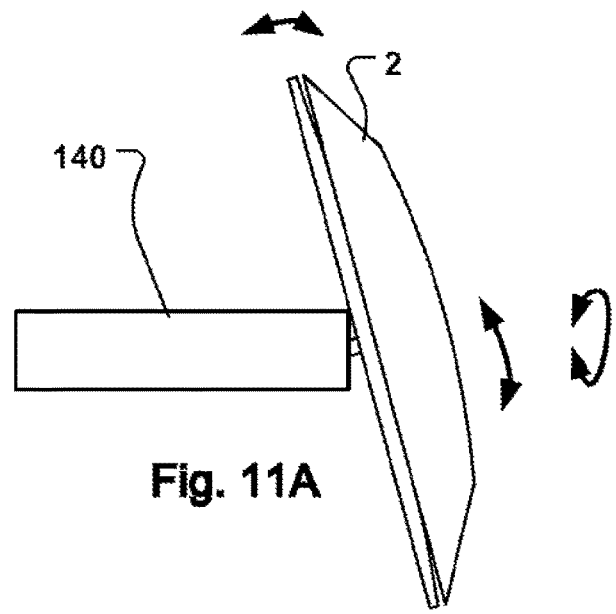
FIG. 11A is a schematic view showing the flexibility in the joint between delivery catheter vs. medical implant.
Figure 11B:
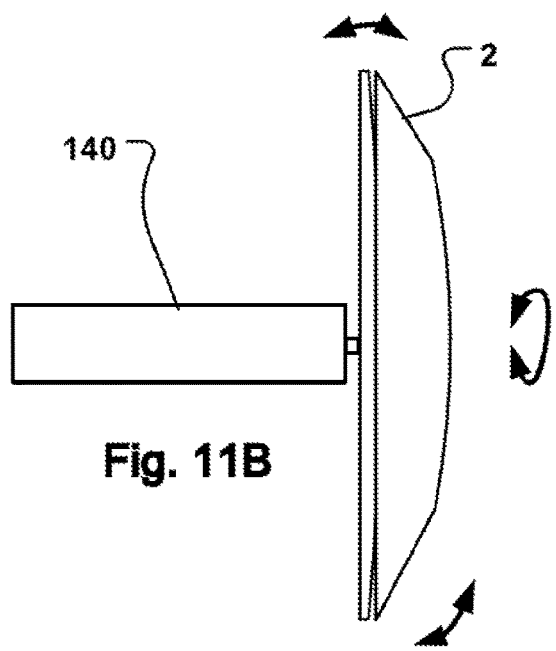
FIG. 11B is a schematic view showing the flexibility in the joint between delivery catheter vs. medical implant.
Figure 11C:
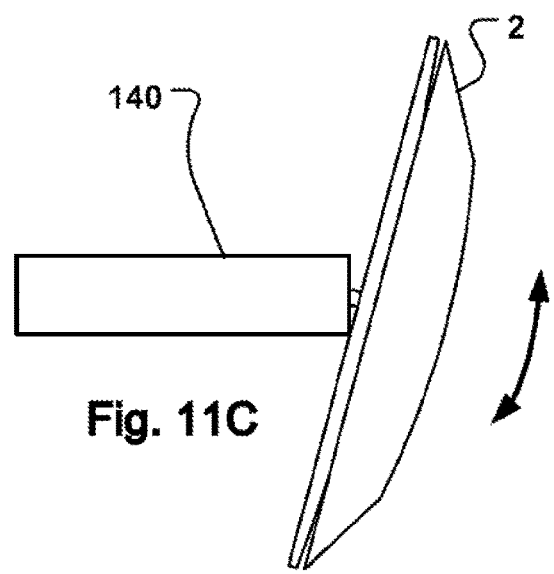
FIG. 11C is a schematic view showing the flexibility in the joint between delivery catheter vs. medical implant.

Loading of the medical implantable device in to the delivery device and locking at the connection interface is e.g. illustrated in FIGS. 7, 9 and 10. The flexibly locked position is shown in FIG. 8.

In an embodiment, the intravascular delivery device comprises a control device connected to the proximal end of the delivery wire for controllably unlocking of the connection interface. Thus may be integrated into a handle for convenient operation. The push operating unit 130 may be operated to move the entire delivery wire with the interlocked medical implantable device 2 at the distal end 10b through a catheter (not shown). When at the target site, and the medical implantable device provided out of the distal end of the catheter, it may be conveniently unlocked for detachment. Locking unit 110 is unlocked. A spring 115 provides a pre-load of the release operating unit 120. The spring may be tensioned against a stop unit 112. Upon pushing against the spring load, the locking wire 150 is pushed in the distal direction and the holding unit is moved out of the distal end 10b. Thus the medical implantable device is released and detached from the delivery device 1.

Figure 4A:
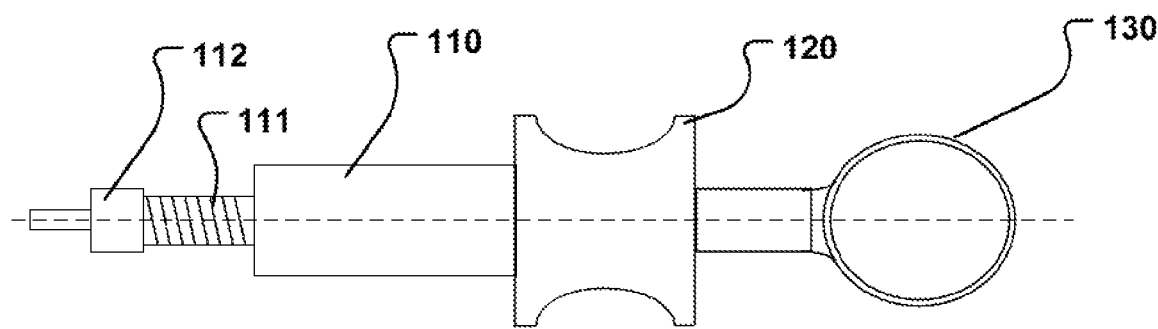
FIG. 4A is an illustration of the device in locked position.
Figure 4B:
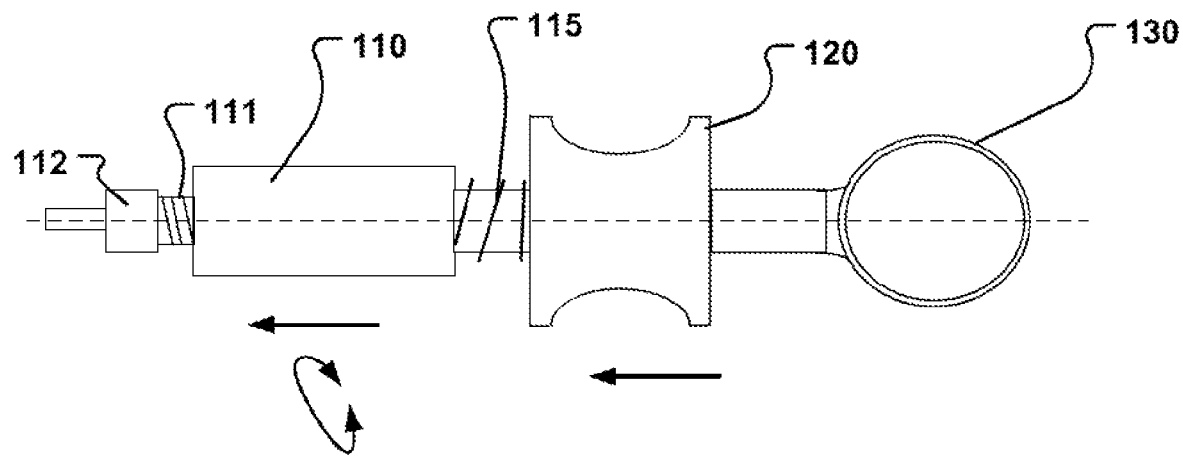
FIG. 4B is an illustration of the device in a releasable position.
Figure 5:
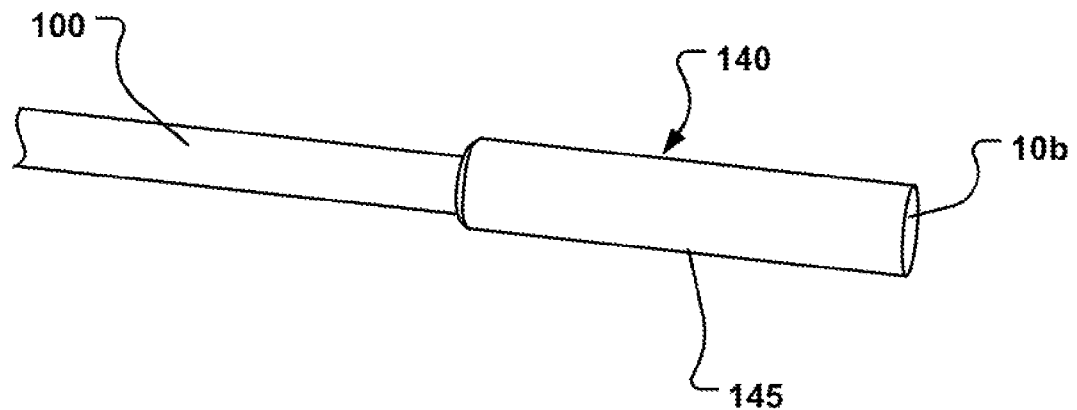
FIG. 5 is a schematic view of the distal tip in a locked position.
Figure 6:
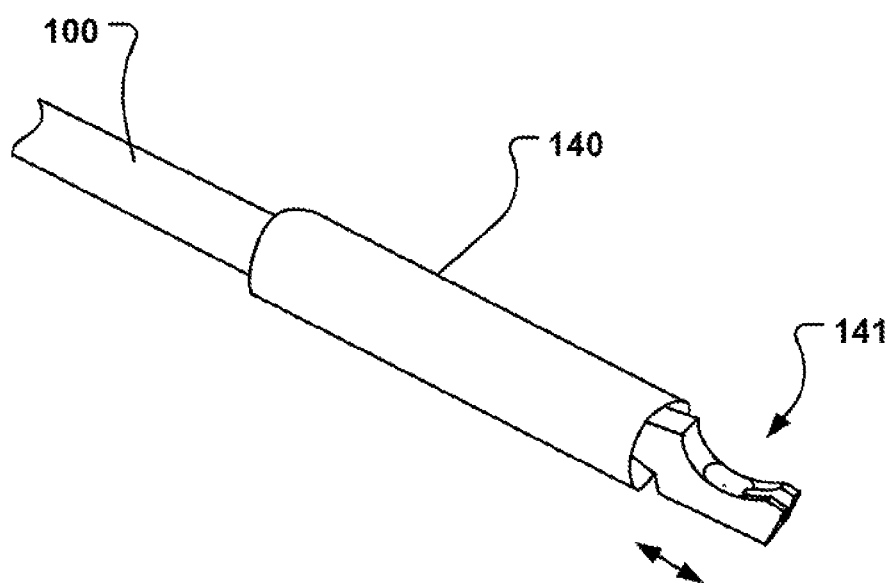
FIG. 6 is a schematic view of the distal tip in the release configuration.

In an embodiment, the control device is secured when the holding structure is in the locking position such that the control device has to be manually operated to allow for the unlocking of the connection interface for controlled release of the medical implantable device from the delivery device, see FIGS. 4A and B.

In an embodiment, a medical implantable device is provided having a proximal end portion adapted to matingly interlock with the connection interface. This is for instance the spherically welded clot of the medical implantable device 2 at the proximal end 200 thereof mating with the spherical recess (bowl-shaped) in the holding unit 141.

Figure 14:
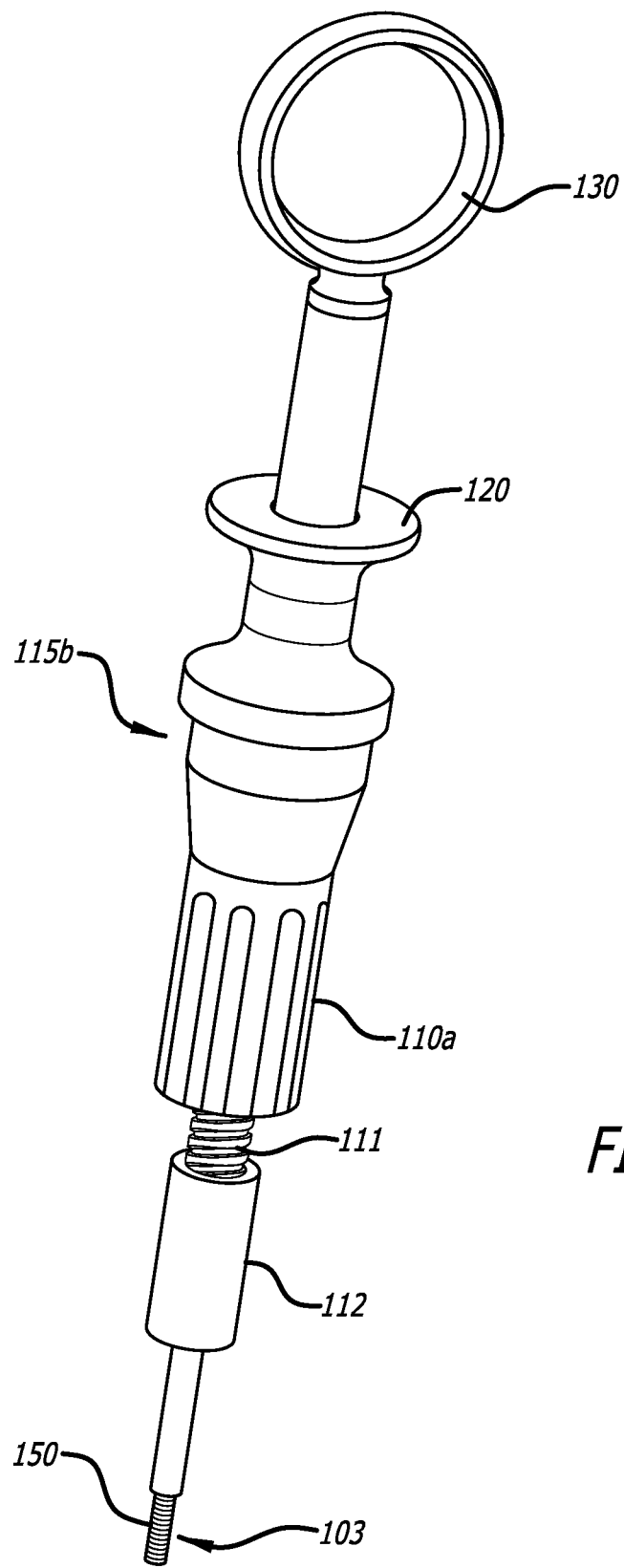
FIG. 14 is a perspective view of a proximal portion of a delivery device having a resiliently flexible unit.

FIG. 14 is a perspective view of a proximal portion of a delivery device having a resiliently flexible unit 115b. The resiliently flexible unit is for instance a disc. The resiliently flexible unit is for instance made of rubber, silicone, or similar materials. Locking unit 110b has a broadened proximal end, in order to provide a larger fitting area to the resiliently flexible unit 115b.

The resiliently flexible unit 115b provides for flexibility of the delivery system even when the holding unit is in the locking position. In this manner, an axial flexibility may be provided when a medical device is locked to the holder unit 141 at the connection interface 140.

Spring 115 provides for a pre-tension of the holding structure 141 in sleeve of the connection interface 140 towards the locking position. This further enhances security of the delivery system. An unintentional loosening of the medical device in the locked position is effectively avoided. Furthermore, when the medical device is positioned in the extended holding structure 141, the holding structure 141 is drawn back into the sleeve of the connection interface 140 when the spindle or release operating unit 120 is released. By screwing the locking unit 110 proximally, the connection interface is secured in the locking position.

The resiliently flexible unit 115b provides in this locking position several advantageous properties.

Figure 15A:
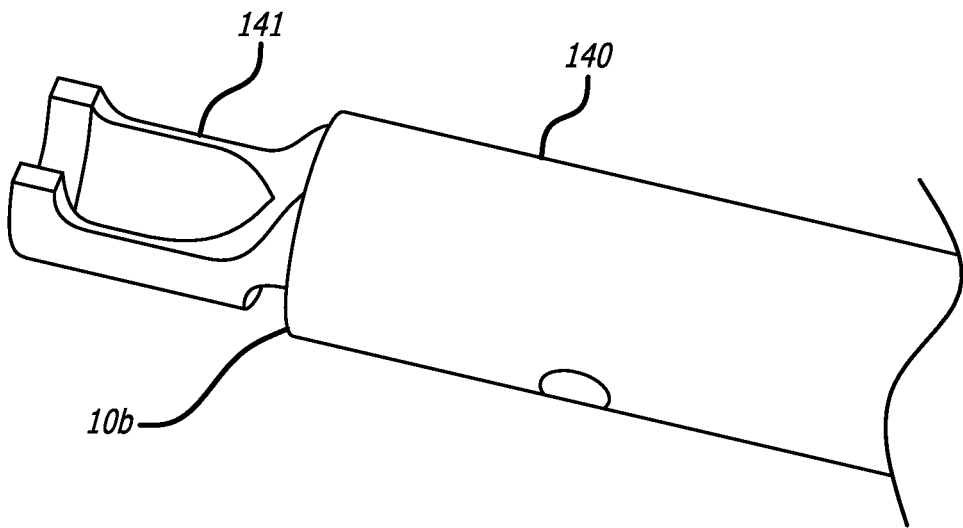
FIG. 15a is an illustration of a holding unit in release position.
Figure 15B:
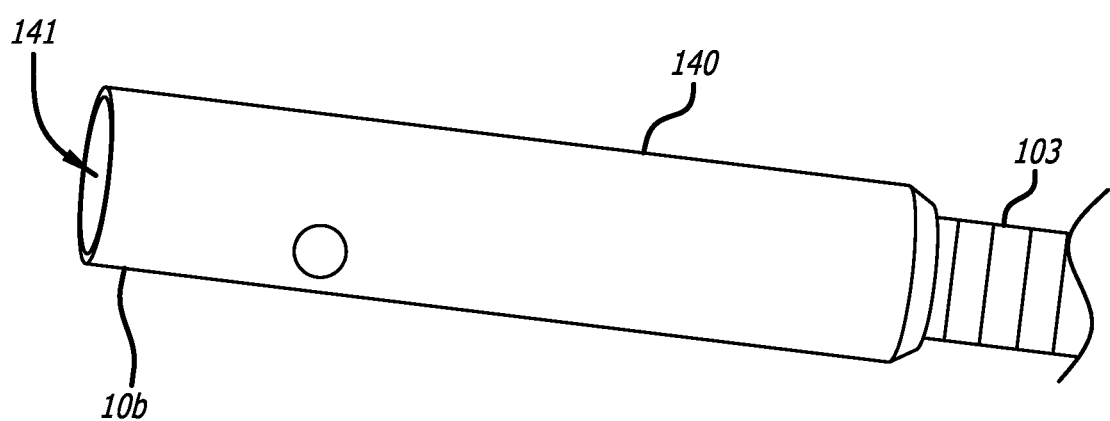
FIG. 15b is an illustration of a holding unit in locking position.

Firstly, a slight axial mobility is provided to the medical device when it is securely locked to the holder unit 141 at the connection interface 140. The axial movement is of course less than holder unit 141 moving out of the sleeve of the holding structure 141. The retracted locking position may also be provided so far in the sleeve of the holding structure 141 that this axial flexibility ends with the distal end of the holding structure 141 flush at the distal end 10b, as shown in FIG. 15b.

Secondly, the entire delivery device is kept flexible during delivery and a tension hardening of the flexible shaft 103. The flexible shaft is wound in form of a spiral. Bending of the flexible shaft is made at a larger radius than bending of the delivery wire 150 in the shaft 103. Forces may be extensive, which may damage the delivery instrument. The resiliently flexible unit 115b solves this issue by providing sufficient flexibility of the delivery device, in particular shaft 103 and delivery wire 150 therein, while securely keeping the medical device attached to the delivery device.

Figure 16:
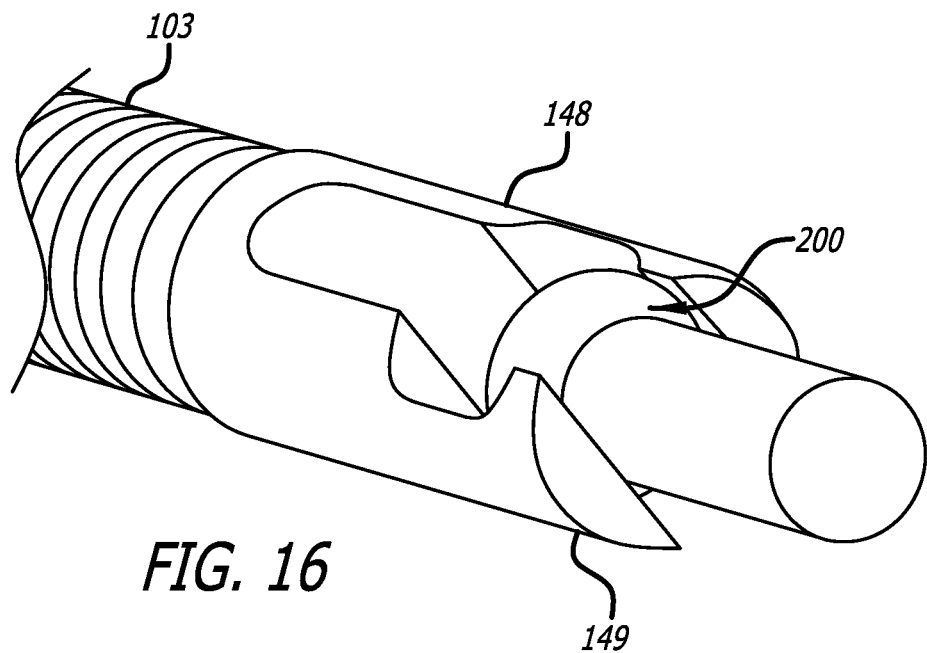
FIG. 16 is a perspective view illustrating another embodiment of the delivery device.
Figure 17:
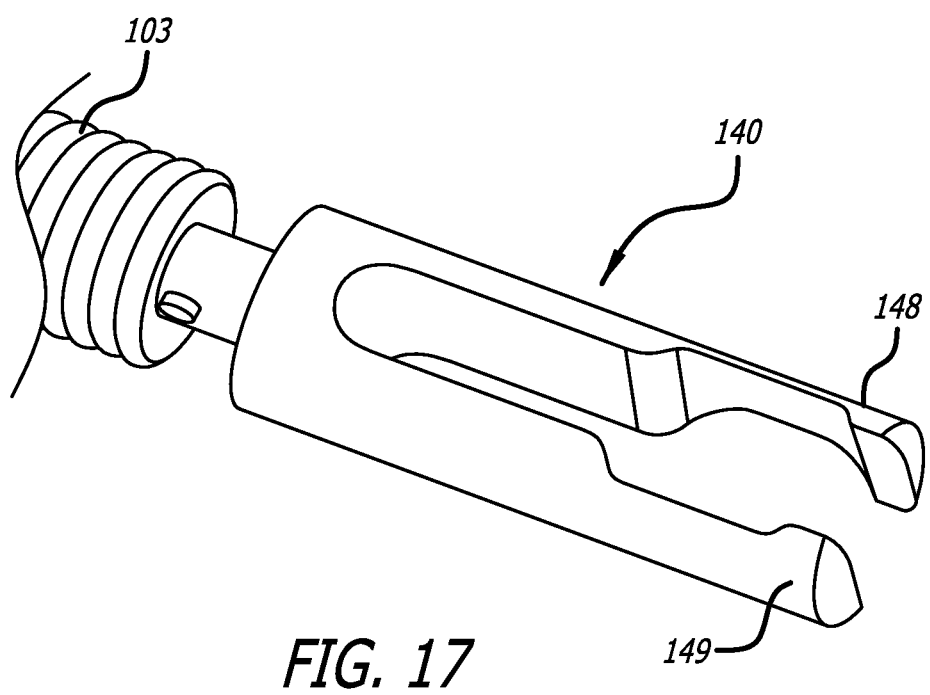
FIG. 17 is a perspective view illustrating another embodiment of the delivery device.
Figure 18:
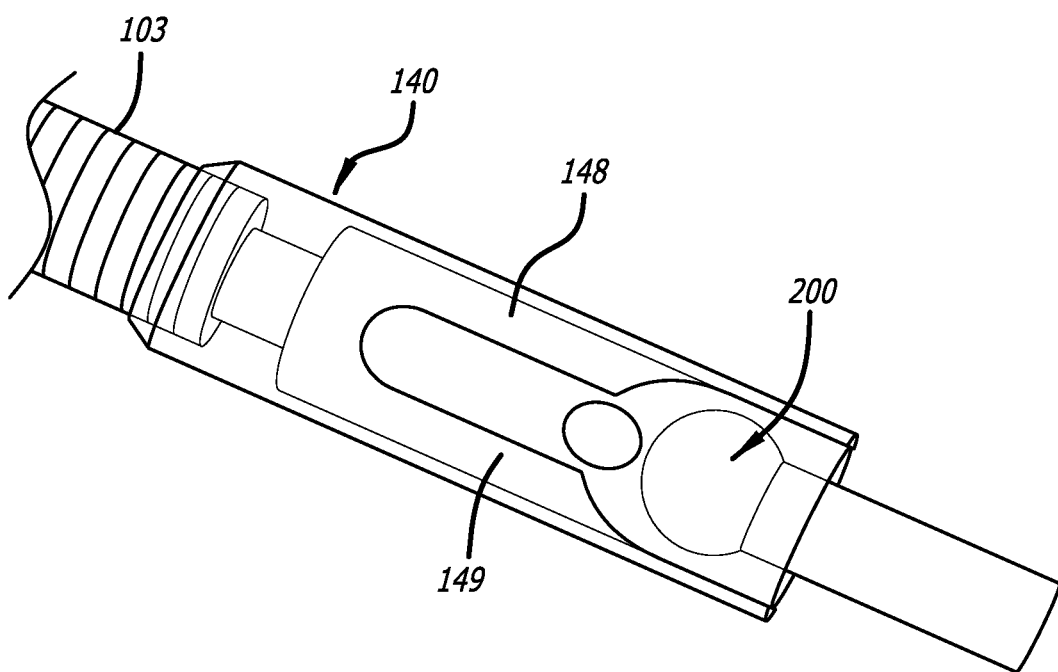
FIG. 18 is a perspective view illustrating another embodiment of the delivery device.

FIGS. 16, 17 and 18 are perspective views illustrating another embodiment of the delivery device. In this embodiment, the holding unit has two longitudinal extensions 148, 149, each having a recess for receiving a spherical end of a medical implantable device, as illustrated. The two longitudinal extensions 148, 149 provide for a slot between the recesses thereof. Loading of the medical device into the delivery device is facilitated as the two recesses of the longitudinal extensions 148, 149 allow for insertion into the slot, and the withdrawing the device into the holding unit 140 and locking the assembly. When the recesses of the two longitudinal extensions 148, 149 are in form of a portion of a sphere, the proximal spherical end of the medical device may be clicked into the slot. It is then withheld therein. Release upon delivery may be made against a counter force provided by the medical implant when anchored at the target site. In addition, the two longitudinal extensions 148, 149 may be provided to expand with their distal ends radially outwardly. The radially outwardly arrangement may be made resiliently. In this manner, the two longitudinal extensions 148, 149 are brought together when drawn into the holding unit 140. Upon pushing the longitudinal extensions 148, 149 out of the holding unit, they radially expand and the slot is made larger, thus releasing a medical implant when delivered. Loading of the medical implant maybe made by inserting the distal spherical end into the slot, pushing the two longitudinal extensions 148, 149 together, and thus holding the implant securely in the spherical recess made up by the recesses in the longitudinal extensions 148, 149. Then drawing the pre-assembly into the holding unit 140 for locking therein is made in a smooth and advantageous way, further improving delivery security of the medical implant while maintaining flexibility of delivery.

In other examples the recesses may be cylindrical and release may thus be made by moving the distal end of the implant sideways out of the slot.

In an embodiment, the medical implantable device comprises a bundle of strands or wires (see FIG. 12), wherein the bundle of strands of the device comprise a welded end having a welded proximal end portion, wherein the welded proximal end portion has defined proportions and dimensions configured as a connection interface adapted to matingly interlock with a holding structure. The medical implantable device may be braided. The proximal end of the medical device has a bundle of parallel strands ending in a welding clot. The welding clot being spherical provides for the ease and flexibility of delivery when using embodiments of the delivery device described herein.

In an embodiment, the connection interface of the medical implantable device has a generally spherical shape.

In embodiments, the connection interface allows for pivotal movement when locked.

In an embodiment, an assembly is provided comprising:
 a delivery device 1 according to above, and
 a medical implantable device 2 according to above, arranged in a catheter for intravascular delivery of the medical implantable device 2.

In an embodiment, the assembly comprises an intravascular delivery device comprising a delivery wire having a proximal and a distal end and an interior lumen extending there between and wherein the distal end comprises a connection interface adapted to matingly interlock with a proximal end portion of a medical implantable device,
 an internal wire extending within the lumen of the delivery wire which is controllable for relative longitudinal movement from the proximal end of the delivery wire, the internal wire having a distal end that carries a holding structure wherein the holding structure is axially moveable relative the delivery wire from a first position at which the delivery wire encloses the holding structure whereby the connection interface is adapted to matingly interlock with the proximal end portion of the medical implantable device to a second position at which the holding structure at least partly protrudes beyond the distal end of the delivery wire such that the connection interface unlocks and the medical implantable device is released;
 a control device connected to the proximal end of the delivery wire;
 a medical implantable device comprising a bundle of strands, the bundle of strands of the device comprising a welded end having a welded proximal end portion, wherein the welded proximal end portion has defined proportions and dimensions configured as a connection interface adapted to matingly interlock with a holding structure, and;
 wherein the medical implantable device is extendable from a relaxed condition capable of assuming a convoluted condition, to an extended, linear condition in which the medical implantable device can be advanced through the lumen of the catheter.

In an embodiment, a method is provided for controlled delivery of the medical implantable device according to above at a selected site in a body vessel. The method comprises:
 introducing a distal end of the above described assembly into a lumen of the body to a delivery site;

releasing the medical implantable device from the distal end of the catheter by pushing the delivery wire distally;

controllably unlocking the medical implantable device from the connection interface by operating the locking unit to unlock, and;

withdrawing the catheter and delivery wire from the body.

The medical implant may be made of a shape memory polymer material.

The medical implant may be made of metal, such as Nitinol.

The retention ball 200 is shaped from laser welded biocompatible Nitinol only, using no other metals. In addition to reducing the amount of material implanted and giving a less traumatic tip, this gives several additional advantages. Most importantly, by not locking the strands at the distal part into a rigid structure, the occluders remain more flexible providing:

Superior adaptation to the septal tissue upon implantation
Superior adaptation to challenging anatomy
Sizing flexibility reducing the number of sizes needed on stock
Softer rims As the occluder device does not have any threaded hub or clamp to provide an attachment for a delivery system. The amount of material implanted in this area is reduced substantially, such as with over 70% by utilizing a specific welding process to form a ball specifically designed for compatibility with the delivery system.

Furthermore, producing a medical implant has been perfected by its Nitinol surface technology to obtain an extremely smooth and flexible outer layer. A golden color of the implant has become synonymous with the highest standard in biocompatibility without risking cracks or deformations forming upon compression/expansion. The composition of the layer is identical to what has been used in 100.000 of Nitinol medical implants with the added advantage of being more flexible.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

What is claimed is:

1. An intravascular delivery device comprising:
a delivery wire having a proximal and a distal end and an interior lumen extending longitudinally therebetween and wherein said distal end comprises a connection interface adapted to matingly interlock with a proximal end portion of a medical implantable device, wherein said delivery device comprises a locking unit arranged to secure said connection interface in a locking position in which a medical implant is pivotably locked before a controlled release such that said medical implantable device is axially and radially pivotable,
a locking wire arranged moveably within the lumen of said delivery wire, said locking wire having a distal end comprising a holding structure,
wherein said holding structure is axially moveable relative said delivery wire between said locking position at which said delivery wire encloses said holding structure and a second position at which said holding structure at least partly protrudes beyond said distal end of said delivery wire such that said connection interface unlocks and said medical implantable device is controllably released.

2. The intravascular delivery device according to claim 1, wherein said connection interface holding said medical implantable device provides for an axial flexibility such that said medical implantable device may tilt relative the longitudinal axis of said delivery device.

3. The intravascular delivery device according to claim 1, wherein said holding structure is radially enlarged to at least partly contact the interior lumen of said distal end of said delivery wire.

4. The intravascular delivery device according to claim 1 comprising a spring arranged to provide for a pre-tension of the holding structure towards said locking position.

5. The intravascular delivery device according to claim 1, comprising a control device connected to said proximal end of said delivery wire for controllably unlocking of said connection interface.

6. The intravascular delivery device according to claim 5, wherein said control device is secured when said holding structure is in said locking position such that said control device has to be manually operated to allow for said controllably unlocking of said connection interface for controlled release of said medical implantable device from said delivery device.

7. In combination, a delivery device of claim 1, and a medical implantable device having a proximal end portion adapted to matingly interlock with said connection interface of said delivery device.

8. The combination of claim 7, wherein said medical implantable device comprises a bundle of strands, said bundle of strands of said device comprising a welded end having a welded proximal end portion, wherein said welded proximal end portion has defined proportions and dimensions configured as a connection interface adapted to matingly interlock with a holding structure, wherein said connection interface has a generally spherical shape.

9. The combination of claim 7, wherein said connection interface allows for pivotal movement when locked.

10. The combination of claim 7 arranged in a catheter for intravascular delivery of said medical implantable device.

11. The intravascular delivery device according to claim 1, comprising a resiliently flexible unit arranged at said proximal end to provide flexibility of said delivery device when said holding structure is in the locking position.

12. The intravascular delivery device according to claim 11, wherein said resiliently flexible unit is a disc.

13. The intravascular delivery device according to claim 11, wherein said resiliently flexible unit is made of rubber or silicone.

14. The intravascular delivery device according to claim 11, wherein said locking unit has a broadened proximal end.

15. An intravascular delivery device comprising
a delivery wire having a proximal and a distal end and an interior lumen extending there between and wherein said distal end comprises a connection interface adapted to matingly interlock with a proximal end portion of a medical implantable device,
an internal wire extending within the lumen of said delivery wire which is controllable for relative longitudinal movement from said proximal end of said delivery wire, said internal wire having a distal end that carries a holding structure wherein said holding structure is axially moveable relative said delivery wire from a first position at which said delivery wire encloses said holding structure whereby said connection interface is adapted to matingly interlock with said proximal end portion of said medical implantable device to a second position at which said holding structure at least partly protrudes beyond said distal end of said delivery wire such that said connection interface unlocks and said medical implantable device is released;

a control device connected to said proximal end of said delivery wire;

a medical implantable device comprising a bundle of strands, said bundle of strands of said device comprising a welded end having a welded proximal end portion, wherein said welded proximal end portion has defined proportions and dimensions configured as a connection interface adapted to matingly interlock with the holding structure, and;

wherein said medical implantable device is extendable from a relaxed condition capable of assuming a convoluted condition, to an extended, linear condition in which said medical implantable device can be advanced through the lumen of said catheter.

16. The intravascular delivery device according to claim 15, wherein said connection interface adapted to matingly interlock with said proximal end portion of said medical implantable device provides for an axial flexibility such that said medical implantable device may tilt relative a longitudinal axis of said delivery device.

17. The intravascular delivery device according to claim 15, wherein said holding structure is radially enlarged to at least partly contact the interior lumen of said distal end of said delivery wire.

18. The intravascular delivery device according to claim 15, comprising a spring arranged to provide for a pre-tension of the holding structure towards said second position.

19. The intravascular delivery device according to claim 15, comprising the control device connected to said proximal end of said delivery wire for controllably unlocking of said connection interface.

20. The intravascular delivery device according to claim 19, wherein said control device is secured when said holding structure is in said first position such that said control device has to be manually operated to allow for said controllably unlocking of said connection interface for controlled release of said medical implantable device from said delivery device.

21. The intravascular delivery device of claim 15, wherein said connection interface allows for pivotal movement when locked.

22. The intravascular delivery device of claim 15, arranged in the catheter for intravascular delivery of said medical implantable device.

23. The intravascular delivery device according to claim 15, comprising a resiliently flexible unit arranged at said proximal end to provide flexibility of a delivery device when said holding structure is in the first position.

24. The intravascular delivery device according to claim 23, wherein said resiliently flexible unit is a disc.

25. The intravascular delivery device according to claim 23, wherein said resiliently flexible unit is made of rubber or silicone.

26. The intravascular delivery device according to claim 23, wherein a locking unit has a broadened proximal end.

* * * * *